United States Patent [19]

Rebour

[11] Patent Number: 4,529,936
[45] Date of Patent: Jul. 16, 1985

[54] SUPPLY CIRCUIT INCLUDING A PAIR OF AMPLIFYING CHANNELS FOR AN EDDY CURRENT PROBE WITH TWO WINDINGS

[75] Inventor: Alain Rebour, Evry, France

[73] Assignee: Intercontrole Societe Anonyme, Rungis Cedex, France

[21] Appl. No.: 465,058

[22] Filed: Feb. 9, 1983

[30] Foreign Application Priority Data

Feb. 10, 1982 [FR] France ................................ 82 02171

[51] Int. Cl.³ ...................... G01N 27/90; G01R 33/12
[52] U.S. Cl. .................................... 324/238; 324/225; 324/232
[58] Field of Search ............... 324/228, 225, 234, 233, 324/238, 62, 227, 232

[56] References Cited

U.S. PATENT DOCUMENTS 3,683,681 8/1972 Van Swaay .
3,895,292 7/1975 Zair et al. .............................. 324/62
3,995,211 11/1976 Yamada et al. ...................... 324/234

FOREIGN PATENT DOCUMENTS 2339170 8/1977 France .

Primary Examiner—Gerard R. Strecker

[57] ABSTRACT

Supply circuit for an eddy current probe with two windings, comprising two parallel supply channels connected to the probe by a cable, each channel incorporating a reference winding and an amplification circuit having an input and an output, one of the ends of the reference winding being connected to the output of the amplification circuit and the other to the input of said circuit via a negative feedback resistor, wherein the amplification circuit of each channel comprises a first amplifier having an input constituting an input of the amplification circuit and an output connected to an absolute measurement access, a first resistor, whereof one end is connected to the output of the first amplifier, a second amplifier having an input connected to the other end of the first resistor and an output constituting the output of the amplification circuit, and a second resistor connected between the output and the input of the second amplifier.

1 Claim, 3 Drawing Figures

SUPPLY CIRCUIT INCLUDING A PAIR OF AMPLIFYING CHANNELS FOR AN EDDY CURRENT PROBE WITH TWO WINDINGS

BACKGROUND OF THE INVENTION

The present invention relates to a supply circuit for an eddy current probe. It is used in the non-destructive testing of metal parts, particularly tubes.

A known eddy current probe supply circuit is shown in FIG. 1. It comprises two channels $10_1$, $10_2$ operating in parallel. Each channel comprises an amplification circuit $12_1$, $12_2$, (which, in the illustrated example, is a differential amplifier), a reference winding $14_1$, $14_2$, and a resistor $16_1$, $16_2$ connected in negative feedback to the amplifierwinding means. Each channel has an input $18_1$, $18_2$ and an output $20_1$, $20_2$. The inputs are connected to a power supply 24, via an amplifier 26 of gain $-1$ for one of them (in the present case input $18_1$ of channel $10_1$). The output of each channel is connected to a coaxial cable $30_1$, $30_2$, supplying a probe formed by two windings $32_1$, $32_2$.

The outputs of amplifiers $12_1$, $12_2$ are connected by two resistors $34_1$, $34_2$. Their center makes it possible to extract a signal on connection D, said signal constituting a differential measurement of the unbalance of the probe. Two other resistors $36_1$, $36_2$ connect the output of one of the channels to the output of the amplifier of the other channel. Their center makes it possible to extract a signal on connection A, said signal constituting an absolute measurement.

This device has the disadvantage of lacking stability as a result of amplifiers $12_1$, $12_2$, which are simultaneously required to supply a high current to the probe and to control the voltage at the probe terminals (high pass band associated with a high output current).

BRIEF SUMMARY OF THE INVENTION

The problem of the present invention is to obviate this disadvantage. For this purpose the amplification circuits are modified. In the prior art, these circuits are formed by a single amplifier $12_1$, $12_2$, which simultaneously performs two functions, namely making the output voltage dependent on the input voltage and supplying the necessary electrical power to the probe. According to the invention, the amplification circuit is constituted by two separate amplifiers, which separately fulfils these two functions, the first controlling the voltage and making it possible to collect an absolute measurement voltage at its output, while the second is used for supplying the probe.

More specifically, the present invention relates to a supply circuit for an eddy current probe having two windings, comprising two parallel supply channels connected to the probe by a cable, each channel incorporating a reference winding and an amplification circuit in the manner described hereinbefore. The amplification circuit of each channel comprises a first amplifier having an input constituting the input of the amplification circuit and an output connected to an absolute measurement access, a first resistor, whereof one end is connected to the output of the first amplifier, a second amplifier with an input connected to the other end of the first resistor and an output constituting the output of the amplification circuit, as well as a secondary resistor connected between the output and the input of the second amplifier.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
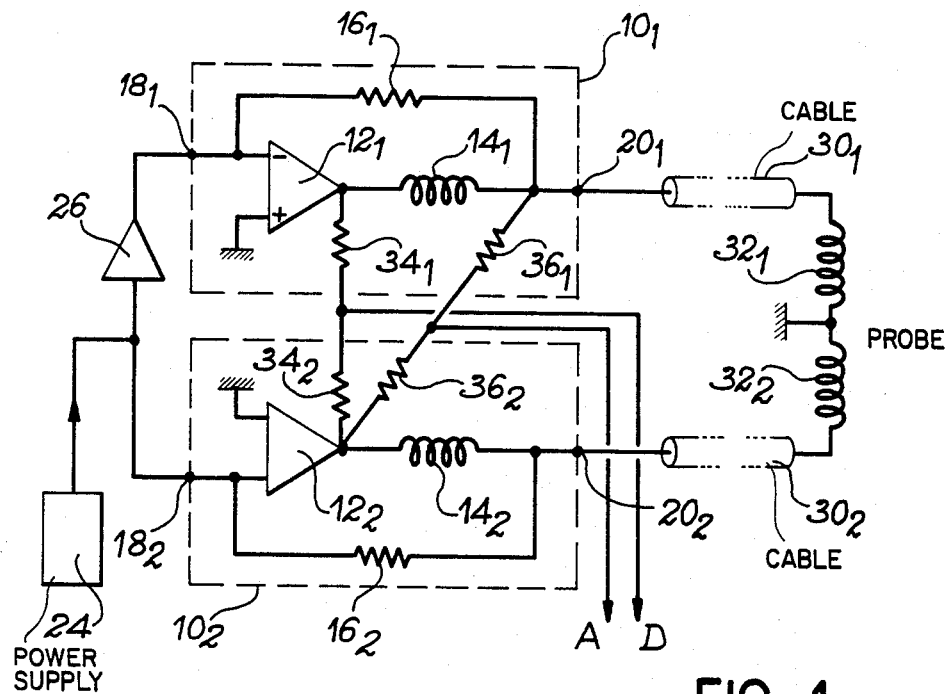
FIG. 1 a known eddy current probe supply circuit.
Figure 2:
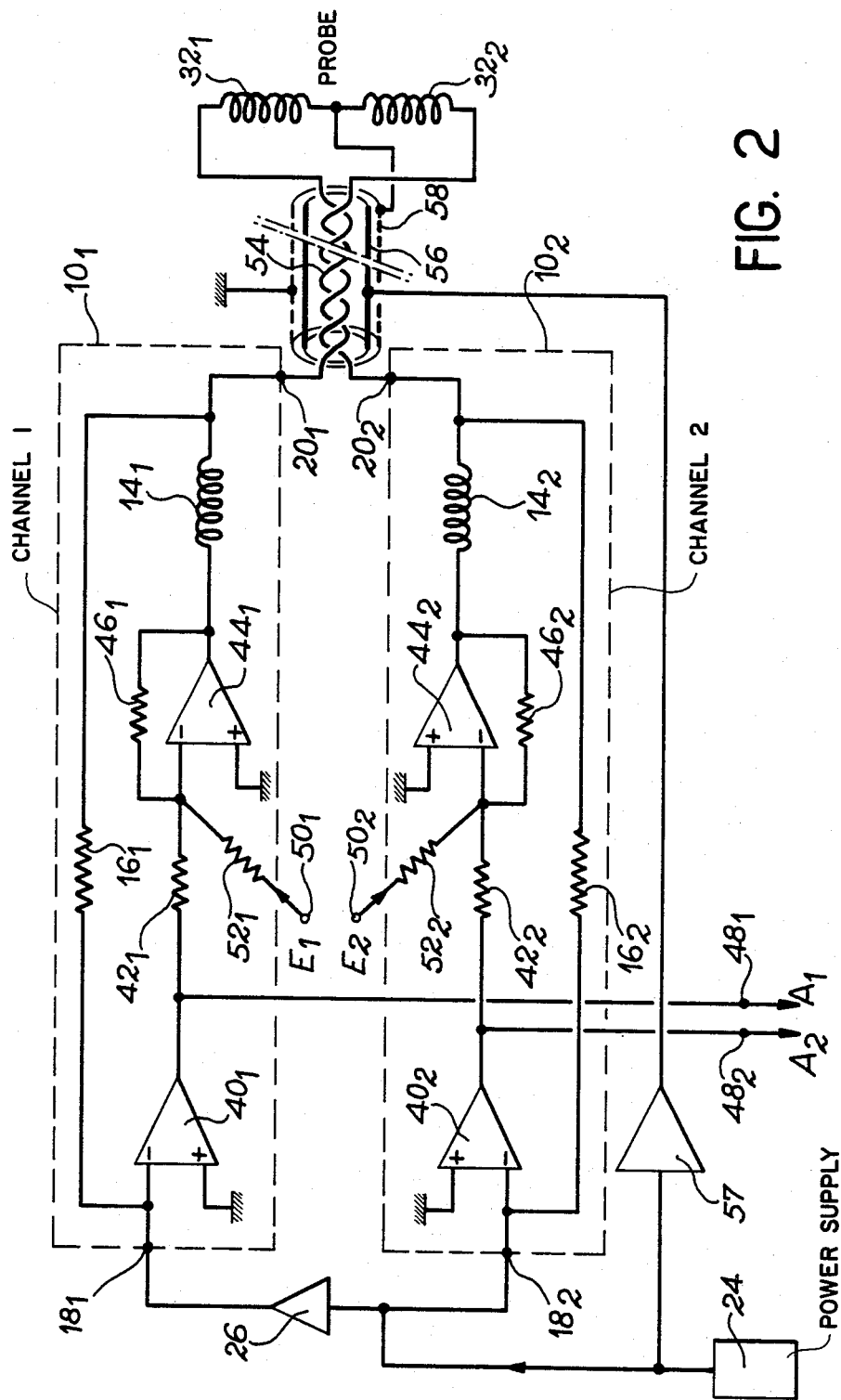
FIG. 2 the general diagram of the circuit according to the invention.

The circuit of FIG. 2 contains the elements already shown in FIG. 1 and which carry the same references. The invention essentially relates to the construction of the amplification means used in each channel. As the means are the same for both channels, the following description will only refer to one of these channels, e.g. the first. The references are then followed by a subscript 1. For the second channels, the equivalent means carry the same references, with a subscript 2.

The amplification circuit of the first channel comprises a first amplifier $40_1$ and gain $-1$. This circuit has an input connected to input $18_1$ of the channel and an output connected to an access $48_1$ at which is available a signal $A_1$. Amplifier $40_1$ can be a differential amplifier having an inverting input and a non-inverting input. The former receives the supply voltage and the latter is connected to earth.

The circuit also comprises a resistor $42_1$ and a second amplifier $44_1$, whose input is connected to said resistor. This amplifier is also of the differential type, with an inverting input connected to resistor $42_1$ and a non-inverting input connected to earth. A resistor $46_1$ is connected between the output and the input of amplifier $44_1$. Moreover, the inverting input of the latter is connected, by a resistor $52_1$, to an access $E_1$ at which can be injected a balancing voltage.

When employing such means, it is amplifier $40_1$ which controls the measuring voltage, whereas the function of amplifier $44_1$ only supplies power to the probe. As a result amplifier $40_1$ has a much better stability than the prior art amplifier $12_1$ which also has to be a power amplifier. Thus, the circuit according to the invention has greater stability.

Thus, the balancing at amplifiers $44_1$ and $44_2$ makes it possible to have two absolute zero measurements at equilibrium, which permits an as high as necessary amplification without any risk of saturation (sensitive absolute measurements) and the possible elimination of filters, when this system is used in multifrequency control.

In the prior art circuit, the two supply outputs of the probe were symmetrical from the potential standpoint. In the system according to the invention, the two outputs $20_1$ and $20_2$ of the two measuring channels are at the same potential. The transmission cable connected to the probe can then be realized by two twisted conductors instead of two coaxial cables, without this leading to a stray capacitance. These conductors can be given a relatively large cross-section, so that the electrical resistance of the cable is reduced. Compared with the prior art, a factor of 10 can be obtained in the cable resistance reduction. The low frequency losses are therefore considerably reduced.

According to this embodiment, the cable is in the form of two twisted wires 54, located within a guard ring 56, connected to the power supply 24 by an amplifier 57. The guard ring is surrounded by a shield 58, connected to earth. The capacitive current supplying the cable is then supplied by amplifier 57, which is not involved in the measurement. The measurement signals $A_1$ and $A_2$ collected at $48_1$, $48_2$ are consequently unaffected by this current.

This arrangment makes it possible to increase the cable length to a considerable extent, without the resistance becoming prohibitive, which is useful when the probe must move in parts located a long way from the measuring means. This is particularly the case in the testing of steam generator tubes in a nuclear reactor.

Figure 3:
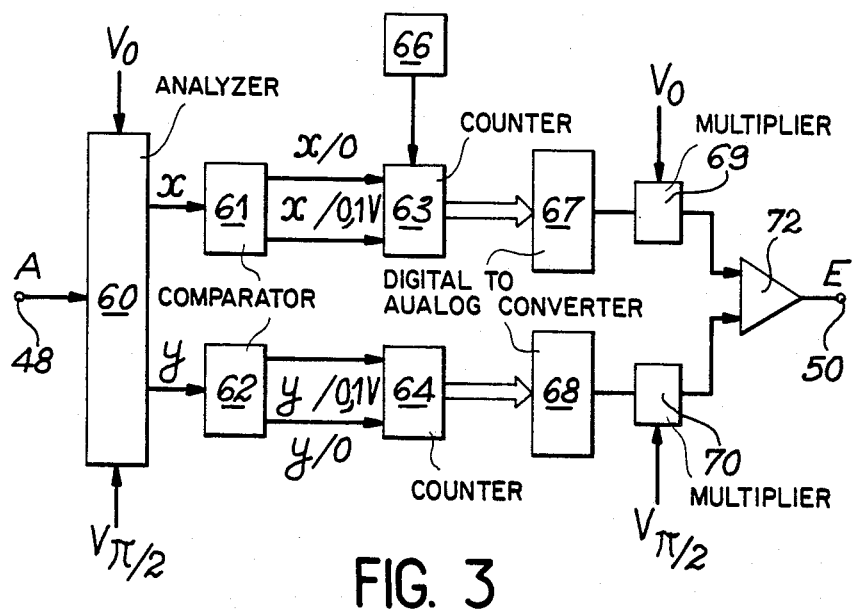
FIG. 3 a balancing circuit.

In the absence of a part to be tested, the measurement signals $A_1$ and $A_2$ need not be strictly zero, due to the unbalances affecting the probe and the circuits. A balancing voltage, able to correct this fault, must then be injected into each channel. These balancing voltages ($E_1$ and $E_2$) are applied to accesses or inputs $50_1$ and $50_2$. A circuit able to produce such voltages is shown in FIG. 3. As it applies to each of the channels, the references are not followed by a subscripted number. This circuit receives a voltage A collected at a terminal 48 (access $48_1$ or $48_2$ in FIG. 2) and supplies a balancing voltage E at terminal 50 (access $50_1$ or $50_2$ of the circuit in FIG. 2). This circuit successively comprises an analyzer 60 receiving a voltage Vo in phase with the supply voltage and a voltage $V_{\pi/2}$ in phase quadrature with this voltage. The analyzer supplies two voltages x and y, which are respectively the components of the input signal in phase and in phase quadrature with the supply voltage. Two comparators 61 and 62 respectively receive the voltages x and y and compare these voltages with two thresholds, one of them being zero and the other low, e.g. 0.1 V. Two signals are emitted by these comparators indicating the respective positioning of x and y relative to these two thresholds. There are two add—subtract counters 63, 64 supplied by a clock 66, two digital—analog converters 67, 68 arranged at the output of the counters, two multipliers 69, 70 respectively receiving the voltages $V_o$ and $V_{\pi/2}$ in phase and in phase quadrature with the supply voltage and an adder 72 having two inputs connected to the two multipliers and to an output constituting the output of the circuit.

Such a circuit is known and it functions as follows. The content of the add—subtract counters varies if the voltages x and y are outside the range defined by the two thresholds, this content increasing if x and y are beyond the high threshold and decreasing if x and y are negative. The content of the counters consequently reflects the value of the digitally expressed unbalance signal. The analog conversion obtained in circuits 67 and 68, makes it possible to supply multipliers 69 and 70, which restore the two components of the correction signal.

What is claimed is:

1. An amplification circuit for use as part of a supply circuit for an eddy current probe with two windings, comprising two parallel amplifying channels, each channel having an input and an output, a cable for connecting the output of each channel to a respective winding of the probe, each channel incorporating a first amplifier having an input constituting an input of the amplification circuit and an output connected to a measurement access terminal for providing a measurement signal, a first resistor having one end connected to the output of the first amplifier, a second amplifier having an input connected to the other end of the first resistor and an output, and a second resistor connected between the output and the input of the second amplifier, a reference winding having a first end connected to the output of said second amplifier and having a second end connected to said output of said amplifying channel, and a third resistor connected between the output and the input of the channel.

* * * * *